US006626847B1

(12) United States Patent
Sjövall

(10) Patent No.: US 6,626,847 B1
(45) Date of Patent: Sep. 30, 2003

(54) METHOD AND APPARATUS FOR MEASURING OF INTESTINAL POTENTIAL DIFFERENCE

(75) Inventor: Henrik Sjövall, Donsö (SE)

(73) Assignee: A+Science Invest AB, Göteborg (SE)

( * ) Notice: Subject to any disclaimer, the term of this patent is extended or adjusted under 35 U.S.C. 154(b) by 0 days.

(21) Appl. No.: 09/787,112

(22) PCT Filed: Oct. 1, 1999

(86) PCT No.: PCT/SE99/01739

§ 371 (c)(1),
(2), (4) Date: Apr. 6, 2001

(87) PCT Pub. No.: WO00/19893

PCT Pub. Date: Apr. 13, 2000

(30) Foreign Application Priority Data

Oct. 6, 1998 (SE) .............................................. 9803375

(51) Int. Cl.⁷ .............................................. A61B 5/00
(52) U.S. Cl. ........................ 600/561; 600/547; 600/587; 600/593
(58) Field of Search ............................... 600/561, 526, 600/481, 480, 485, 547, 587, 593; 128/898

(56) References Cited

U.S. PATENT DOCUMENTS

| | | | | |
|---|---|---|---|---|
| 4,030,485 A | * | 6/1977 | Warner | 600/480 |
| 4,429,701 A | * | 2/1984 | Goor et al. | 600/526 |
| 4,798,211 A | * | 1/1989 | Goor et al. | 600/481 |
| 4,821,735 A | * | 4/1989 | Goor et al. | 600/526 |
| 5,551,425 A | | 9/1996 | Essen-Moller | |
| 6,158,438 A | * | 12/2000 | Shen | 128/898 |
| 6,261,235 B1 | * | 7/2001 | Amano et al. | 600/485 |
| 6,364,842 B1 | * | 4/2002 | Amano et al. | 600/485 |
| 6,485,431 B1 | * | 11/2002 | Campbell | 600/526 |

OTHER PUBLICATIONS

Wingate, D.L., "The measurement of transmural potential difference in the intact human proximal small intestine," J. Physiol, Jun. 1973, vol. 231, No. 2, pp. 95P and 96P.

Scarpignato, C. et al., "Transmucosal Potential Difference as an Index of Esophageal Mucosal Integrity", Digestion 1995, vol. 56, Suppl 1, pp. 51 to 60. (1995 S.Karger AG, Basel 0012–2823/95/0567–0051 $8.00).

* cited by examiner

*Primary Examiner*—Teresa Walberg
*Assistant Examiner*—Fadi H. Dahbour
(74) *Attorney, Agent, or Firm*—Burns, Doane, Swecker & Mathis, L.L.P.

(57) ABSTRACT

The present invention relates to a method and apparatus for producing a transmucosal potential different (PD) signal essentially being unaffected by intestinal motor activities. This is accomplished by reducing the PD signal based on time variations in the intraluminal pressure (IP) signal. The invention also relates to different applications of such a signal, such as measurement of the total peripheral resistance (TPR), detection of abnormalties in the enterical nervous system, detection of damages in the mucosal barrier.

25 Claims, 4 Drawing Sheets

METHOD AND APPARATUS FOR MEASURING OF INTESTINAL POTENTIAL DIFFERENCE

FIELD OF THE INVENTION

The present invention relates to a method and an apparatus for producing a transmucosal potential difference (PD) signal essentially being unaffected by intestinal motor activities. It also relates to different applications of such a signal.

BACKGROUND OF THE INVENTION

All human tissues are depending on a continuous supply of blood to survive. The tissues control their own supply of blood by releasing substances to expand or contract the nonstriated muscle of the incoming blood vessels. However, these blood vessels also take part in the overall blood pressure regulation, being controlled by the central nervous system (CNS). This regulation works on the principle of maintaining the arterial pressure as constant as possible, which for instance is crucial for the kidneys to work optimally. The human body can modify the mean arterial pressure (MAP) in two ways: by changing the total throughput in the system, which is the cardiac output (CO), i.e. the total blood quantity that the heart pump per time unit, or by changing the total peripheral resistance (TPR), i.e. the total vascular resistance in the system. The following relation for the parameters hold:

$$MAP = CO \times TPR$$

It can clearly be seen by the above-mentioned relation, that if the MAP is falling and the CO is essentially constant at a normal level, the problem must be in the TPR, and the compensation is to enhance the CO. If, on the other hand, the CO is not constant, but on a low level, the compensation is to enhance the TPR. The body "measures" the MAP directly by means of pressure receptors on the arterial side, and the CO with knowledge of the heart frequency, filling pressure and contractility. With the knowledge about CO and MAP the body can "calculate" the TPR and compensate accordingly when the MAP is falling.

In the intensive care it is very common that one or several of these parameters are deranged, and it is of crucial importance for the correct treatment to be aware of the problem. The intensive care physicians have medicines at hand to affect the CO as well as the TPR, and to be able to use these medicines correctly he needs information about at least two of the parameters in the above-mentioned equation. It is, however, difficult, if at all possible, with the current techniques to obtain a continuous registration of anything but the MAP. Access to a continuous recording system is crucially important since it gives the possibility of an "alarm-function" which alerts the physician to initiate early compensatory interventions.

The CO can be measured intermittently by introducing a so called PA catheter into the pulmonary artery and estimating the CO from the time-temperature curve of a supplied "cold pulse", a so called thermodilution principle. However, there are several drawbacks with this method, and it is only used in the most severe cases. Moreover, the measurement only gives a momentarily on-the-spot measure, and the measurement can not be repeated more than a few times. Furthermore, catheterization of the heart adds a small but significant risk for complications in these severely ill patients.

There is, as far as the applicant is aware of, no known method to directly measure the TPR with full time resolution. In clinical routine, this parameter is usually only roughly estimated by a subjective evaluation of skin temperature to be "peripherally warm" or "peripherally cold".

There is consequently a strong need for a preferably non-invasive method that continuously measures the TPR. A continuous signal would not only make it possible to alert the physician to make early interventions when the patient deteriorates, but could also be used to quantitatively optimize volume substitution, cardiotropic drugs etc.

The most important regulation mechanism for TPR is the activity in the sympathetic nervous system, and one of the most important vascular beds controlled by this system is the gastrointestinal tract, which thus is very important in the blood-pressure regulation.

Intestinal vasoconstriction can, however, also be potentially detrimental, since it can cause damage to the mucous membrane, and render it possible for bacteriaes to translocate to the blood side, which may in turn lead to severe toxaemia, i.e. blood poisoning. If this sequence of events is not detected in time, it is often too late to save the patient's life. Therefore, there is a strong need for a method for measuring intestinal sympathetic activity not only as an indirect measure of the TPR, but also to diminish the risk for mucosal damage and bacterial translocation.

The transmucosal potential difference (PD) signal reflects the potential generated by chloride secretion in the mucous membrane in the intestine. The principle behind the PD-measurement is illustrated in FIG. 1. Active secretion of chloride, which occurs via a specific ion channel, the CFTR, generates a current across the mucosa that recirculates through the paracellular shunt resistance. The transmucosal potential difference (PD) will consequently depend on both the rate of chloride secretion and the magnitude of the shunt resistance. In isolated tissue in vitro, the ionic current can be measured by short-circuiting the tissue with an external current source, in which case the shunt current becomes zero. The current needed for short-circuiting the membrane, the short-circuit current (SCC), is consequently identical to the membrane current. In vivo, short-circuiting is obviously impossible.

Typical examples of the SCC and PD signal and the effect of sympathetic activation in vitro, i.e. in the absence of motor activity, is shown in FIGS. 2a–d.

Hence, the size of the PD signal depends on a number of factors, reflecting the condition for the intestinal functions, such as salt transportation ability for the mucous membrane, an undamaged mucosal barrier, correctly working neurogenic control of the epithelium, and level of sympathetic activity. The PD signal is possible to measure relatively easily by the introduction of a thin plastic tube into the upper part of the bowel, and measurement of the potential difference between a perfusion and a similar solution infused subcutaneously. However, a problem with this PD signal is that it is also strongly affected by the intestinal motor activities, i.e. the peristalsis. The magnitude of these changes is relatively large, and it has therefore hitherto been nearly impossible to sort out the sympatethic component of the signal in the presence of intestinal motor activity, and for this reason the PD signal has never actually been applied in clinical practice.

SUMMARY OF THE INVENTION

It is therefore an object of the present invention to provide a method and an apparatus for producing a transmucosal potential difference (PD) signal that is essentially unaffected by intestinal motor activities and which therefore reflects intestinal sympathetic activity and TPR. It is also an object of the invention to provide some applications of such a signal.

This object is achieved by the invention such as it is defined in the enclosed claims.

SHORT DESCRIPTION OF THE DRAWINGS

For exemplifying purposes, the invention will be described in closer detail in the following with reference to embodiments thereof illustrated in the attached drawings, wherein.

Figure 3A:
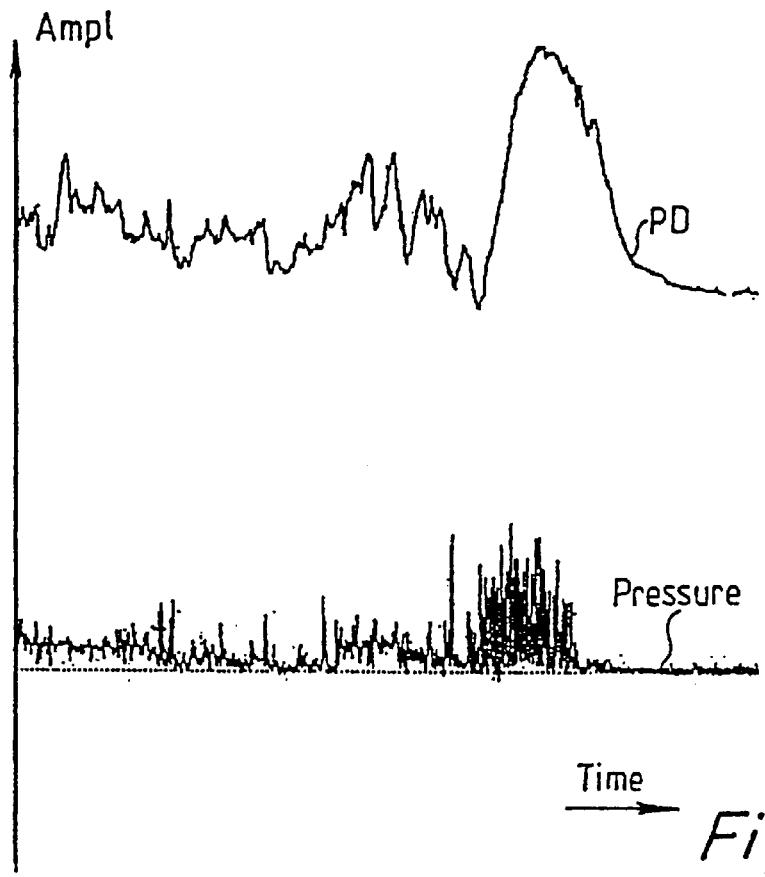

FIG. 3a gives an example of a non-filtered PD curve recorded in vivo and a corresponding pressure curve.

Figure 3B:
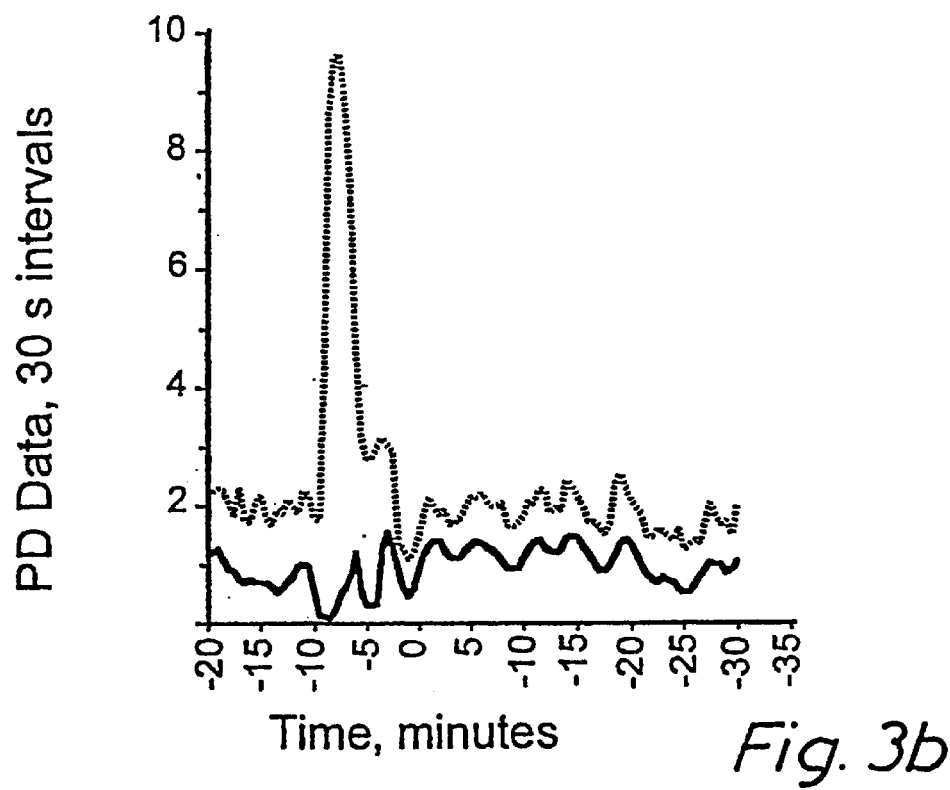

FIG. 3b is an example of a reduction of a PD signal according to the invention.

DESCRIPTION OF PREFERRED EMBODIMENTS

According to the invention a potential difference (PD) signal is measured, by means of a PD measuring device which is introduced into the intestine. The principle of the measurement is that the potential difference between the electrolyte solution that is infused into the intestine, and the same solution infused subcutaneously, is measured by a specially constructed amplifier. Such measuring devices are previously known; e.g. a Grasspolygraph from Grass instruments, MA, USA and a Pressure transducer from Statham instruments, CA, USA could be used. To minimize electrical "noise", the signal has to be filtered according to established principles which will not be described in further detail in this application.

Further, an intraluminal pressure (IP) signal is measured in the intestine by measuring inflow pressure on the same fluid column as the one used for PD recording, i.e. at exactly the same mucosal site. The IP signal is obtained by means of a pressure sensor, which is also known in the prior art.

The IP-signal registers the muscular contractions of the bowel. However, these contractions also activate nerve endings in the intestinal ganglion system, leading to activation of an intramural reflex, which in turn stimulates electrogenic chloride secretion. Accordingly there is a change in the PD signal as well, in association with the contraction. There are, however, important dynamic differences between the two signals. The IP signal is almost instantaneous, whereas the PD signal has a maximum rising rate, which is dependent on the secretion capacity of the mucous membrane. Accordingly, the PD signal can only be increased at a certain maximal rate, independent of the strength of the stimulation. More important for the PD signal level is the duration of the contraction, i.e. during how long time the increase of the signal will last.

After the pressure wave there is a decrease in the PD signal, with an approximately mono exponential time course.

An important feature of the pressure-PD linkage is that it is dependent on frequency rather than amplitude. Due to the "slowness" of the PD signal, each isolated supra threshold pressure wave (which has a duration of less than 5 seconds) will give rise to a PD deflection which will be the maximal rate of rise of the PD signal multiplied by the duration of the contraction. However, this relationship does not apply if another contraction occurs before the PD response has had time to decay. Instead, at high contraction frequencies the PD response to isolated waves are superposed, i.e. added "on top" of each other, which gives rise to a PD increase which greatly exceeds that generated by an individual contraction, irrespective of its amplitude.

The wave duration and frequency in the IP signal is therefore of much greater importance in evaluating the PD signal than is the amplitude of the pressure waves.

During repeated contractions the PD signal eventually reaches a maximum level, and after this level there will not be any further increase in the PD signal, independent of any further stimulation from contractions and pressure waves. This maximum level for the PD signal is typically reached after around twelve pressure waves at the maximum frequency. The maximum level for the PD signal varies between individuals, and is dependent on the maximum secretion capacity of mucous membrane, and is therefore linked to the maximum rising rate.

When the PD signal has reached the maximum level there will be a so called escape phenomenon, and the signal will start to fall, largely independent of any further phasic pressure waves. This decrease of the signal strength from the maximum level will typically be in the form of a mono exponential function. However, also during this escape period, an increase of the mean pressure in the bowel will generate an increase in the PD signal (probably by stimulation of a different receptor population). The dependence of the mean pressure, i.e. the gain in response to a certain increase in the mean pressure to the PD signal, varies between individuals, and is preferably determined in each individual subject.

In the method according to the present invention both the PD signal and the IP signal are measured with the appropriate measuring devices, and then the PD signal is reduced from the signal components originating from the pressure variations in an evaluating device. This reduction is made according to the principles described above. The reduction is performed in an evaluation device, connected to the measuring devices, which e.g. could be an application specific integrated circuit or a conventional personal computer. The reduction is preferably digitally executed, and if necessary the signal from the measuring devices are analog-to-digital converted.

The PD signal is mainly reduced based on the time variations in the IP signal. At first the PD signal is reduced with a reduction for every single wave in the pressure signal. The reduction for every wave is essentially the duration of the wave times the maximal rise ratio, which is preferably determined for every patient. By this step alone the influence of the pressure variation on the PD signal is greatly diminished.

Between the pressure waves the reduction is diminished, and preferably in a mono exponential manner.

Further, a maximal reduction value is determined, beyond which no further reduction of the PD-signal should be made. This value could either be determined directly or derived from the therewith associated maximal rise ratio. When the reduction value comes close to this maximum reduction value, the additional contributions to the reduction from the pressure waves are preferably diminished, typically in an essentially mono exponential manner, so that the reduction never can exceed the maximum reduction value.

Then, after the reduction has reached, or at least almost reached, the maximum reduction value, the reduction is again decreased, preferably in a mono exponential way. This is the so-called escape phenomenon, and this effect dominates over any further reduction caused by the pressure waves, at least for some time.

However, if there is an increase in the mean pressure, this will affect the reduction, and cause an increased reduction, irrespective of the escape phenomenon. An increased mean pressure will therefore result in an increased reduction, whereby the reduction is the mean pressure change times a determined gain constant. A decrease in the mean pressure will accordingly result in a reduced reduction of the same magnitude.

Naturally the PD signal can also preferably be filtered to remove electrical artifacts and noise, in a manner that is obvious for someone skilled in the art.

The remaining filtered and reduced PD signal is essentially unaffected by intestinal motor activities, and provided that the mucosal barrier is intact, it is possible to deduce from this signal the level of sympathetic activity, which in turn quantitatively reflects the TPR.

In FIG. 3a is shown an example of a PD signal recorded in vivo in a fasting subject. As is clearly seen, there is a pronounced variation in this signal, which contrasts to the in vitro situation. Further, a simultaneous pressure recording from the same subject is shown. As can be seen, increases in the motor activity are associated with large increases in the PD signal.

In FIG. 3b is shown an example of reduction of a large-amplitude PD deflection by means of the method according to the invention which is described above. In this figure the original PD signal is shown with a dashed line, and the filtered signal with a unbroken line.

If the mucosal barrier becomes damaged, i.e. if the parallel resistance over which the current generated by chloride secretion is shunted decreases, the PD value may decrease independently of sympathetic nerve activity. This may in turn lead to erroneous interpretation resulting in inappropriate treatment. It is therefore important to include in the measuring device an independent measuring system which detects changes in mucosal parallel resistance. This is done by generating an "artificial" electrochemical potential difference across the mucosa and measuring continuously the ability of the mucosa to maintain this potential. The "artificial" PD is preferably generated by perfusing another port of the same catheter, opening at some distance ($\approx$5 cm) from the pressure-PD-port, with a solution containing an electrolyte solution in which sodium and chloride have been substituted with mannitol, an inert sugar. The mannitol in the lumen will "drag" water and electrolytes through negatively charged pores in the paracellular channels, and will generate a lumen positive luminal potential, a so called streaming potential.

Figure 1:
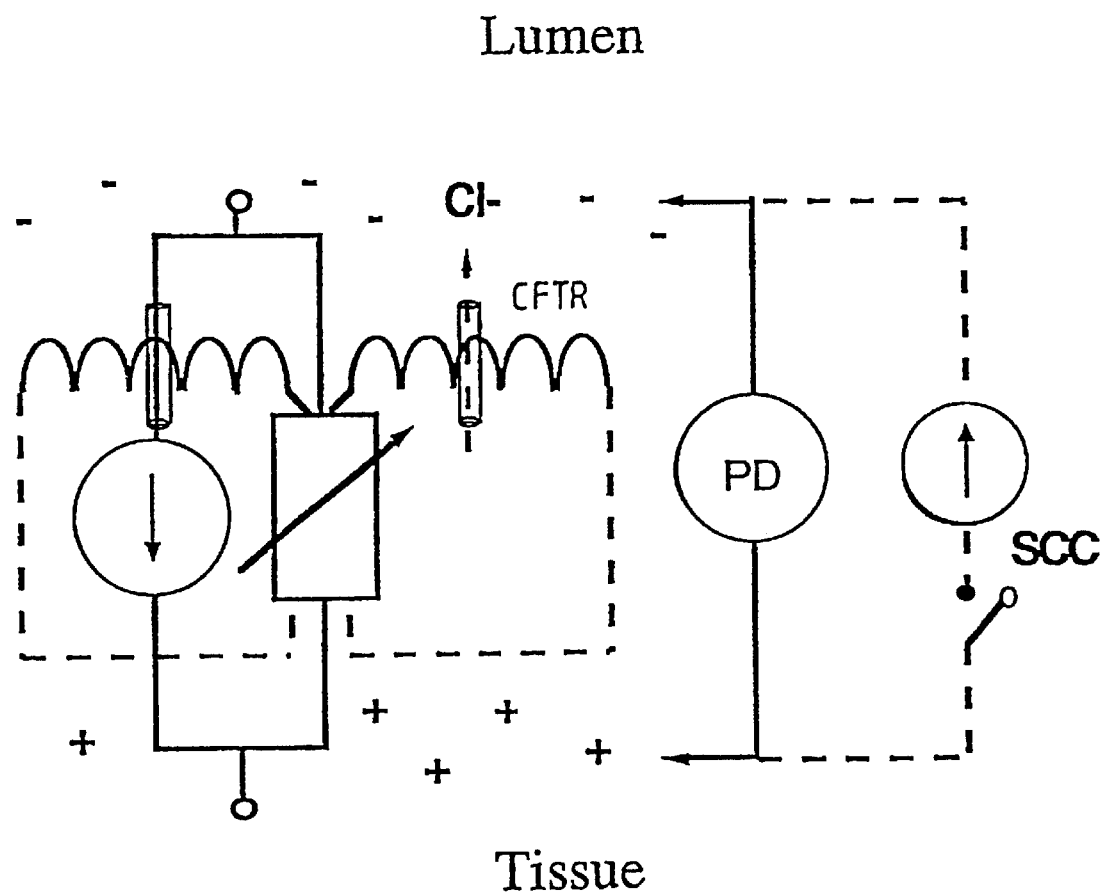
FIG. 1 is an schematic illustration of the principle behind PD-measurement.
Figure 2A:
FIG. 2a is an example of a SCC signal measured in vitro. The arrow in the figure shows the effect of noradrenaline, the sympathetic signal substance.
Figure 2B:
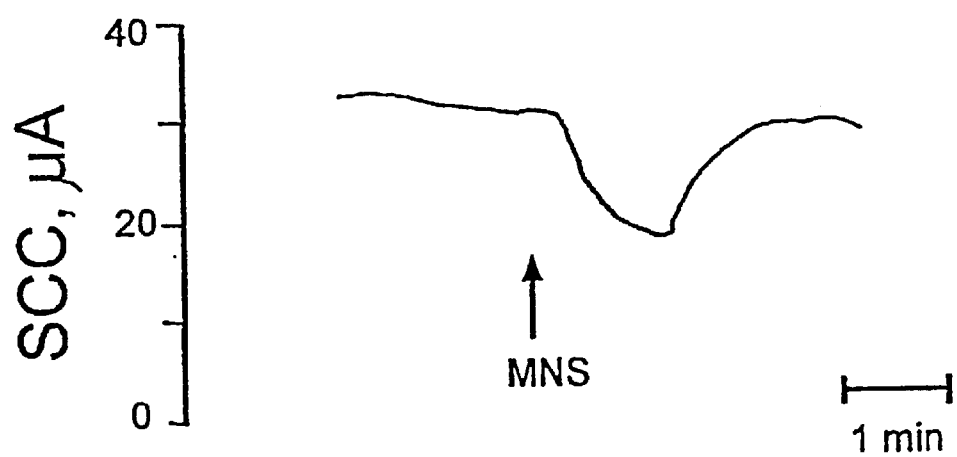
FIG. 2b is an example of electrical activation of sympathetic neurons on SCC in vitro, where the arrow indicates the MNS (mesenteric nerve stimulation).
Figure 2C:
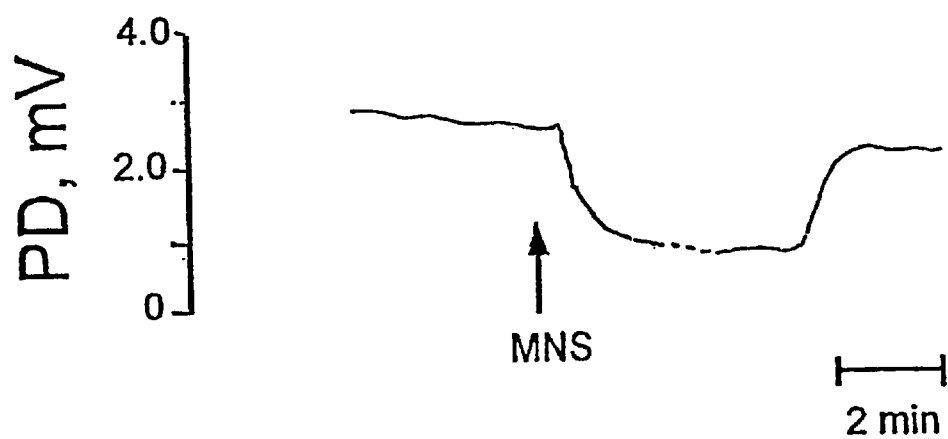
FIG. 2c is an example of a "stable" PD signal recorded in isolated intestine, without disturbing motor activity. The arrow in the figure shows the effect of sympathetic nerve stimulation (MNS).
Figure 2D:
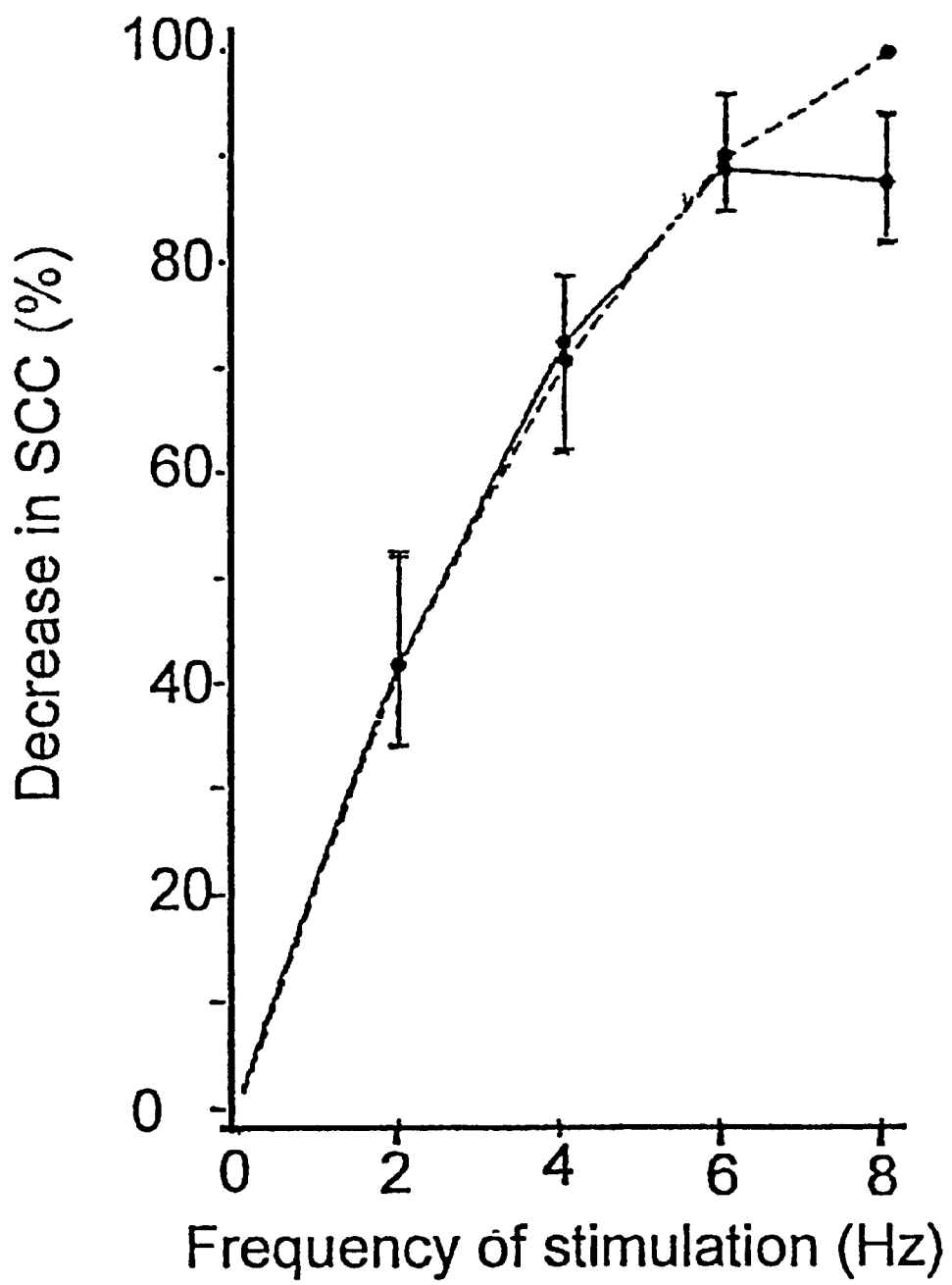
FIG. 2d is an example of a frequency-response curve of sympathetic effect on SCC in vitro.

This "artificial" ion current is similar to the ionic current that can be measured in isolated tissue in vitro (see FIG. 1) by short-circuiting the tissue with an external current source. However, in this case, an artificial ion current is instead generated by changing the composition of the perfusate. The difference between this "artificial" PD generated by this current and the spontaneous PD will hence be an indirect measurement of the magnitude and ion selectivity of the shunt resistance. If the shunt resistance decreases or if there is damage to the membrane, the "spontaneous" and artificial signals will become identical. This means that if the passive electrical behaviour of the membrane deteriorates, the membrane will be unable to generate and maintain this potential, and the magnitude of the positive potential will diminish. The streaming potential phenomenon will consequently be "superimposed" on the normal PD changes induced by motor activity, and therefore have to be reduced in the way already described.

With this two-point-recording, it is thus possible to judge if a decrease in the "reduced" PD signal is due to an increased sympathetic activity in a healthy, ion-selective mucosa, or is due to a deterioration of the passive ion-selective properties of the membrane. With an intact mucosal barrier, the method and apparatus according to the invention thus give the desired continuous signal reflecting intestinal sympathetic nerve activity and, indirectly, TPR. If the reduced PD value decreases without signs of impaired mucosal barrier, the physician can take appropriate measures to reduce sympathetic activity, e.g. by increasing volume substitution etc. This is exceedingly important, since the next stage of deterioration is damage to the mucosal barrier, which may in fact be generated by excessive sympathetic activation. By including the "artificial potential" function, one can therefore also include an alarm function for early signs of membrane deterioration, which immediately have to be treated vigorously since a broken membrane barrier may lead to bacterial invasion with a high risk for so called "irreversible shock", a very common cause of death in intensive care units.

All neuronal structures are highly sensitive to hypoxia and if the oxygen supply to the intestine becomes seriously disturbed, the function of the intestinal ganglia therefore rapidly deteriorates. The "reduction function" for the PD signal is based on an intact function of the enteric neurons, more particularly an intact linkage between the myenteric and submucous plexa. If this linkage mechanism becomes disturbed, i.e. if contractions no longer give rise to the expected PD deflections, this may be another, independent marker for intestinal hypoxia. The clinical occurrence of this phenomenon has not been much studied since no methods have so far been available, but it seems exceedingly likely that changes in the dynamic behaviour of the pressure-PD linkage can be an independent early marker for enteric neuronal dysfunction. The invention will therefore also include an alarm function which is activated if the pressure and PD signals do not dynamically correlate in the expected manner.

With such a combined measurement simultaneous information is obtained of an indirect measure of TPR, an continuous measure of the electrical resistance in the mucous membrane and regarding a number of parameters reflecting the condition of the function of the enteric nervous system. For all these measures the measurement could be continuous, and alarm limits could easily be provided to automatically alert medical personnel in case of emergency.

What is claimed is:

1. A method for producing a preferably continuous transmucosal potential difference (PD) signal essentially being unaffected by intestinal motor activities, characterised by the steps of:

measuring the intestinal potential difference (PD);

measuring the intraluminal pressure (IP) in the intestine; and reducing the PD signal based on the time variations in the IP signal.

2. A method according to claim 1, wherein the reduction is based on the duration of waves in the IP signal and the time between the waves.

3. A method according to claim 2, wherein the PD signal is based on a constant reduction for the duration of the waves, the constant reduction being determined by a predetermined limit value for the maximal PD enhancement.

4. A method according to claim 3, wherein two or more waves having a time distance between them that is shorter than a predetermined threshold value is considered as one single wave with a duration being the sum of the duration of the actual waves.

5. A method according to claim 2, wherein the reduction is diminished between the waves, preferably in the form of a monoexponential function.

6. A method according to claim 5, wherein the reduction is diminished, preferably following a monoexponential function, when the reduction is at or at least near the maximal reduction value.

7. A method according to claim 1, comprising the step of determining a maximal reduction value, beyond which no further reduction of the PD-signal should be made.

8. A method according to claim 1, wherein the reduction further is based on the mean value of the IP signal.

9. A method for measuring the total peripheral resistance (TPR), characterised by the steps of:
   obtaining a transmucosal potential difference (PD) signal essentially without affection from intestinal motor activities, according to the method in claim 1;
   obtaining, from this PD signal, a quantitative signal that reflects the TPR.

10. A method according to claim 9, including the initial step of measuring the mean arterial pressure (MAP) and the cardiac output (CO) and determine a calibration value for the TPR as MAP divided by CO.

11. A method for detecting abnormalities in the enterical nervous system, characterised by the steps of:
   obtaining a transmucosal potential difference (PD) signal and analyze it according to the method defined in claim 1;
   determine whether the connection between the PD signal and the IP signal is abnormal; and
   in case of abnormality automatically give an alarm warning for abnormalities in the enterical nervous system.

12. Method according to claim 11, wherein the connection between the PD signal and the IP signal is considered abnormal when the potential difference (PD) signal essentially being reduced from affection from intestinal motor activities shows one or both of a negative value or top values exceeding a predetermined threshold value.

13. An apparatus for detecting abnormalities in the enterical nervous system, characterised by means for obtaining a transmucosal potential difference (PD) signal and analyzing it according to the method defined in claim 1, evaluating means for determining whether the connection between the PD signal and the IP signal is abnormal; and alarm-means which are automatically activated by the evaluating means in case of abnormality to give an alarm warning for abnormalities in the enterical nervous system.

14. A method for detecting damages in the mucosal barrier, characterised by the steps of:
   obtaining a transmucosal potential difference (PD) signal essentially without affection from intestinal motor activities, to the method in claim 1;
   obtaining an artificial potential difference (APD) signal, likewise essentially without affection from intestinal motor activities, according to the method in claim 1, generated by a potential measurement with a perfusion with an ionic concentration different from that used in the PD-measurement, and preferably comprising sugar such as glucose or mannitol;
   obtaining a mean difference value between the PD and the APD signal; and
   detecting a damage in the mucosal barrier when said difference value is lower than a predetermined threshold value.

15. A method according to claim 14, comprising the additional step of in case of a detected damage automatically give an alarm.

16. An apparatus for detecting damages in the mucosal barrier, characterised by means for obtaining a transmucosal potential difference (PD) signal essentially without affection from intestinal motor activities, according to the method in claim 1; means for obtaining an artificial potential difference (APD) signal, likewise essentially without affection from intestinal motor activities, according to the method in claim 1, with use of a perfusion with an ionic concentration different from that used in the PD-measurement, and preferably comprising sugar such as glucose or mannitol; means for obtaining a mean difference value between the PD and the APD signal; and means for detecting a damage in the mucosal barrier when said difference value is lower than a predetermined threshold value.

17. An apparatus according to claim 16, whereby the means for measuring the PD and the APD signal comprises one common catheter, comprising two separate channels debouching at some distance apart at the distal end of the catheterer, and preferably about 5 cm apart.

18. An apparatus for producing a transmucosal potential difference (PD) signal essentially being unaffected by intestinal motor activities characterised in that it comprises a device for measuring the intestinal potential difference (PD), a device for measuring the intraluminal pressure (IP) in the intestine and an evaluation device, with inputs connected to the measuring devices, for reducing the PD signal based on the time variations in the IP signal, and with an output to supply the reduced PD signal.

19. An apparatus according to claim 9, wherein the reduction is based on the duration of waves in the IP signal.

20. An apparatus according to claim 10, wherein the evaluation device is adapted to reduce the input PD signal based on a constant reduction for the duration of the waves, the constant reduction being determined by a predetermined limit value for the maximal PD enhancement.

21. An apparatus according to claim 19, wherein the reduction is diminished between the waves, preferably in the form of a monoexponential function.

22. An apparatus according to claim 18, whereby the evaluation device is adapted to have a maximal reduction value, beyond which no further reduction of the PD-signal should be made.

23. An apparatus according to claim 22, wherein the reduction is diminished, preferably following a monoexponential function, when the reduction is at or at least near the maximal reduction value.

24. An apparatus according to claim 18, wherein the reduction further is based on the mean value of the IP signal.

25. An apparatus for registering changes in the total peripheral resistance (TPR), characterised in that it comprises means for obtaining a transmucosal potential difference (PD) signal essentially without affection from intestinal motor activities, according to the apparatus in claim 18, and evaluating means for estimating, from the PD signal, the TPR.

* * * * *